United States Patent [19]
Nicolesco

[11] Patent Number: 6,147,357
[45] Date of Patent: Nov. 14, 2000

[54] APPARATUS AND METHOD FOR INSPECTING THE EDGE MICRO-TEXTURE OF A SEMICONDUCTOR WAFER

[75] Inventor: Claudian R. Nicolesco, Portland, Oreg.

[73] Assignee: Wacker Siltronic Corporation, Portland, Oreg.

[21] Appl. No.: 09/243,962

[22] Filed: Feb. 3, 1999

[30] Foreign Application Priority Data

Feb. 5, 1998 [EP] European Pat. Off. .............. 98101958

[51] Int. Cl.⁷ .................................................. G01N 21/88
[52] U.S. Cl. .................... 250/559.46; 250/228; 356/371; 356/237.2; 356/236; 348/128; 348/131
[58] Field of Search .............................. 250/228, 559.46; 348/86, 87, 126, 128, 131; 356/236, 371, 237.2, 237.3, 237.4, 237.5

[56] References Cited

U.S. PATENT DOCUMENTS 5,461,417  10/1995  White et al. ............................ 348/131

*Primary Examiner*—F. L. Evans
*Attorney, Agent, or Firm*—Collard & Roe, P.C.

[57] ABSTRACT

An apparatus and a method are provided for inspecting the edge micro-texture of a semiconductor wafer. The apparatus includes a diffuse hemisphere having at least one access port and has a normal axis, a laser target sphere mounted within the hemisphere, and a laser source directing a laser beam to the laser target sphere and forming a laser spot on the laser target sphere. The laser beam is reflected from the laser target sphere. A wafer chuck presents a wafer edge to the reflected laser beam, with the wafer edge being tilted from the normal axis; and there is at least one camera for detecting radiation leaving the access port. The method includes directing a laser beam to a laser target sphere which is mounted within a diffuse hemisphere; the laser beam forming a laser spot on the laser target sphere is reflected from the laser target sphere to the edge of a wafer; and radiation which leaves the hemisphere through at least one access port of the hemisphere is detected with at least one camera.

13 Claims, 2 Drawing Sheets

APPARATUS AND METHOD FOR INSPECTING THE EDGE MICRO-TEXTURE OF A SEMICONDUCTOR WAFER

BACKGROUND OF THE INVENTION

1. Field of the Invention

The present invention relates to the visual, non-contact edge inspection of semiconductor wafers, e.g. silicon wafers, at different stages of wafer processing such as slicing, lapping, edge-shaping (grinding), etching, and polishing which is generally performed by trained operators. The inspection occurs under a bright light, from halogen or fluorescent lamps, with the naked eye, or by using a magnifier lens (2× to 4× magnification).

2. The Prior Art

In this type of inspection, the submilimetric size of some edge defects makes inefficient the visual inspection with the naked eye.

A better alternative to such methods would be to perform the inspection with a video camera microscope with a special illumination light source. This light source can be a gooseneck fiber or a fiber optic ring attached parallel and coaxial to the camera objective.

Most wafer edge inspection equipment currently available uses video cameras with the microscope objective attached. Also there are visible, fluorescent or halogen lamps (Hologenix), or red laser beams (Champman), which are used as light sources for detecting/monitoring the defects and characterizing the edge texture roughness.

For these instruments, the light beam impinges upon the wafer edge surface at one particular angle, 90 degrees or less. The reflected light that contains the wafer edge texture information is then captured by the video camera.

Generally speaking, the wafer edge illumination methods fall in two categories: 1) dark-field illumination (DF) and 2) bright-field illumination (BF). A bright-field illumination system examines directly reflected light (close to the normal incidence beam), while a dark-field illumination system examines light scattered off the wafer (under small angle incidence beam), almost parallel with the edge.

Bright-field illumination means illuminating the edge at normal incidence angle, and looking at the resulting reflected image. This configuration can be described as a "co-axial" or "through-the-lens" geometry because the light source has a solid angle with respect to the part being observed. For example, a 25 mm light source (laser or light bulb), at a distance of 100 mm from the part being imaged, has a solid angle approximately equal to arctan $25/100=14$ degrees.

For flat specular surfaces, such as polished flat edges, the minimum dimension for a light source WBFmin, held at a distance $D=(D1-D2)$ of the camera lens, should be twice the field-of-view width V, plus the camera lens entrance pupil diameter (aperture) A (FIG. 1).

Then, to completely fill the field-of-view on a planar, normally viewed specular object with uniform light, the BF coaxial illuminators should be larger than and external to the camera lens.

When a specular surface deviates from planar, as in a real beveled edge, for each one degree of full range of surface angle variation, the solid angle of the illumination source must be increased by double in order to appear fully and uniformly illuminated. For example, if a surface has +/−N degree of variance for a total range of 2N degree variance, the total solid angle of light source must be increased by 4N degree, and its diameter from WBFmin to WBF (FIG. 2).

Dark-field illumination uses light impinging upon the object at oblique low angles, and there is detection of the scattered or diffracted rays from the inspected surface, outside the direct specular field-of-view.

This method is used to obtain information primarily from the scratches and particles that have a very small cross-section when inspected under normal angle, but increase their scattered cross-section at low angles. Since the dark-field uses scattered light, this method does not resolve the real size of the defect. This is because at this angle the incident spot size of the laser on the surface can be much larger than the smallest detectable defect.

If the bright-field illuminator has its solid angle of illumination extended to the horizon in all directions, covering practically the dark-field also, the result would be a solid hemisphere. This solid hemisphere includes both the specular and the scattered rays, with very small incident angles, almost parallel to the inspected surface. In the natural world, such continuous uniform illumination geometry is never achieved unless no observer is present. This is because the observer inevitably creates a discontinuity into the field surrounding the object under observation.

In this case, there is a continuous diffuse illumination, inside of a hemisphere. This is a theoretical, ideal, uniform, omnidirectional light source, known in optics as Coblenz sphere or "Total Integrated Sphere" (TIS) illuminator.

U.S. Pat. No. 5,461,417 discloses a practical "Continuous Diffuse Illumination" (CDI) light source, based on this TIS principle.

The basic feature of this prior art U.S. patent is the combination of a diffuse on-axis light source with adjacent off-axis light sources of equal brightness impinging light onto a diffusive hemisphere, to create a continuous diffuse illumination field.

The CDI, described in this prior art U.S. patent, can create a continuous uniform diffuse illuminator if both the on-axis and off-axis light sources are active, at the same time. If only one light source is on, then the, CDI changes itself into in a bright-field illuminator, when only the on-axis source is on. Also the CDI will change itself into a dark-field illuminator, when only the off-axis sources are on. It needs not only an extra mirror-like beamsplitter for separating the bright-field light rays from the reflected light incoming from the inspected sample. But it also needs a minimum of two extra dark-field light sources to be installed inside the diffusive hemisphere. A light switch between these BF and DF sources can only deliver light beams with fixed directions, diameters, and a specific power ratio.

SUMMARY OF THE INVENTION

It is an object of the present invention to provide an apparatus and a process for inspecting the edge micro-texture of a semiconductor wafer based on a TIS laser source.

The apparatus of the invention for inspecting the edge micro-texture of a semiconductor wafer comprises a diffuse hemisphere having at least one access port and defining a normal axis; a laser target sphere mounted within the hemisphere; a laser source directing a laser beam to the laser target sphere and forming a laser spot on the laser target sphere, said laser beam being reflected from the laser target sphere; a wafer chuck presenting a wafer edge to the reflected laser beam, said wafer edge being tilted from the normal axis; and at least one camera for detecting radiation leaving the access port.

The process of the invention comprises directing a laser beam to a laser target sphere which is mounted within a diffuse hemisphere; said laser beam forming a laser spot on the laser target sphere and reflecting the laser beam from the laser target sphere to the edge of a wafer; and detecting radiation which leaves the hemisphere through at least one access port of the hemisphere with at least one camera.

BRIEF DESCRIPTION OF THE DRAWINGS

Other objects and features of the present invention will become apparent from the following detailed description considered in connection with the accompanying drawings which disclose a few embodiments of the present invention. It should be understood, however, that the drawings are designed for the purpose of illustration only and not as a definition of the limits of the invention.

In the drawings.

DETAILED DESCRIPTION OF PREFERRED EMBODIMENTS

Figure 1:
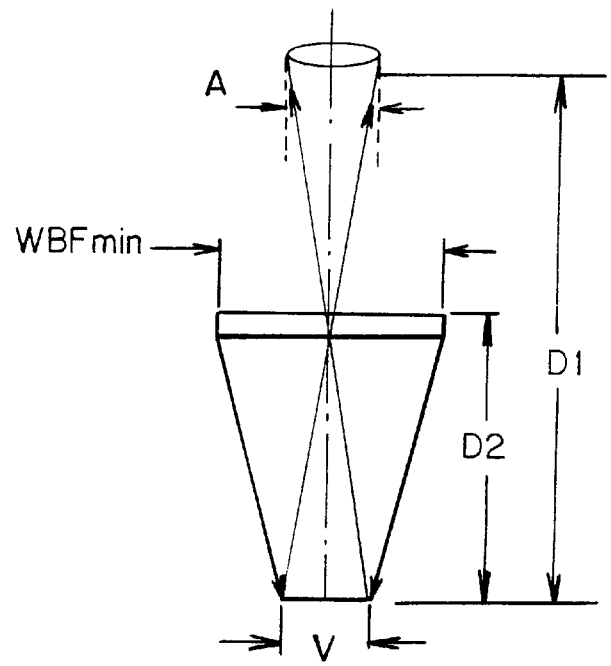
FIG. 1 shows prior art apparatus for minimum dimension bright field illumination WBFmin.
Figure 2:
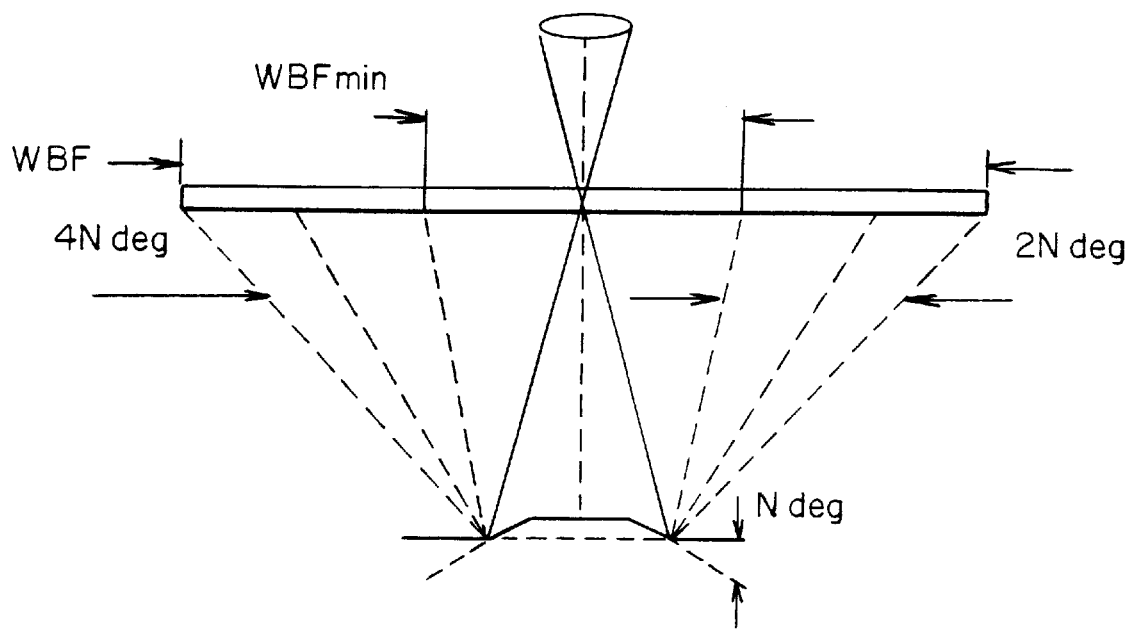
FIG. 2 shows prior art apparatus for beveled edge bright field illumination WBF.
Figure 3:
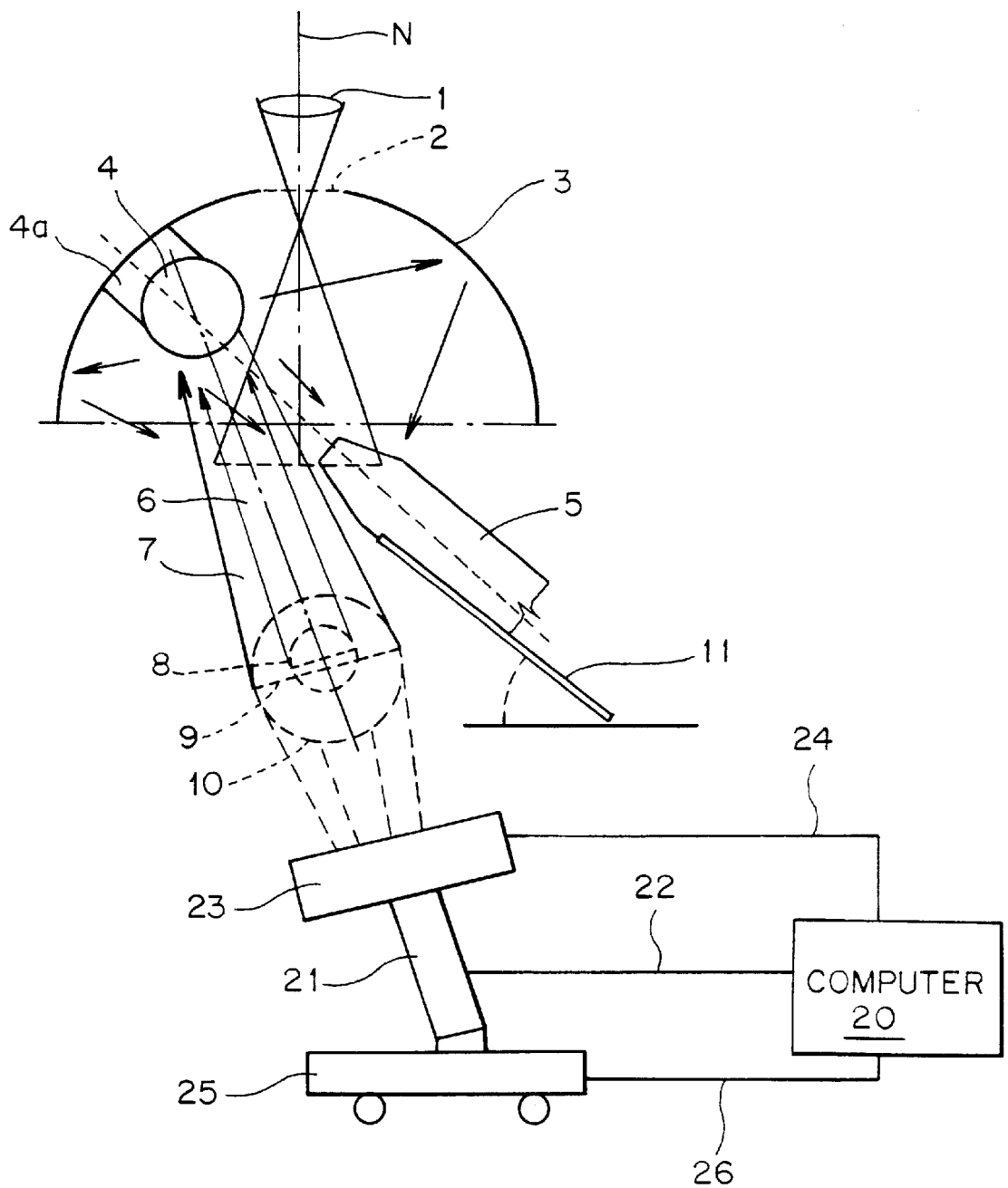
FIG. 3 shows a preferred embodiment of the apparatus of the invention, namely a "Continuous Diffuse Variable Field Laser Illuminator" (CD-VELI).

Turning now in detail to the drawings, FIG. 3 shows that the apparatus of the invention comprises a diffuse hemisphere 3 having a central access port 2 for a video camera 1, and an internal diffuse laser target sphere 4, mounted at 45 degrees from the camera port 2. Means 4a is used for mounting the laser target sphere 4 on hemisphere 3. It is also possible to provide more than one access port and one camera, e.g. two access ports and two cameras.

The inspected wafer 5 is positioned under the hemisphere 3 at preferably 45 degrees from the normal axis N. This permits a better edge inspection angle, in order to get an evenly focused magnified image of the edge bevel. The wafer will be mounted on vacuum chuck 11 that can be tilted eventually away from the 45 degree position with a gimbal platform, and rotated with a rotary stage.

A laser beam 10 has a variable beam diameter, and has a variable cross-section pattern, such as a solid circle or an annular-hollow circle. Laser beam 10 will impinge upon the target sphere 4 at a variable incidence angle (around 45 degrees from the normal axis N) and will be reflected toward the wafer 5 and toward the hemisphere 3. The focused laser beam spot can be moved on the target 4, or outside it, on the hemisphere 3.

Changing the laser beam diameter, its cross-section pattern, or moving the laser spot position on the target sphere 4 or on the hemisphere 3 will continuously change the illuminator characteristic from bright-field only to dark-field only or to TIS. Thus, by refocusing the laser beam 10, which impinges upon the laser target sphere 4, from BF 6 to DF 7, one can continuously modify the characteristics of the illumination light source. Therefore, the light source can be modified from a bright-field source only (if the laser beam diameter is limited to WBFmax 8), to a dark-field source only (if an annular beam pattern is selected, with a diameter between WBFmax 8 and WDFmax 9). The light source can also form a continuous diffusive uniform light source TIS (if the circular laser beam has a larger diameter than WDFmax 9 and reaches the diffuse hemisphere 3).

A second possibility for changing the illuminator characteristics is to keep the laser beam diameter/pattern unchanged, but move the laser focused spot on the laser target sphere. This will produce a variable angle of incidence of the reflected rays impinging upon the examined sample and thusly changing the source characteristic from a bright-field to a dark-field, or to TIS.

By means of computer 20, it is possible to control laser source 21 over lead 22 and to control lens optical system 23 for the laser over lead 24 and to control laser transport mechanism 25 over lead 26. Computer 20 can be programmed so as to cause optical system 23 to vary the diameter of the laser beam emitted by laser 21. Computer 20 can also cause optical system 23 to vary the cross section pattern of the laser beam 21. The computer can cause mechanism 25 to move the laser spot on the laser target sphere 4 or on the hemisphere 3.

Accordingly, while a few embodiments of the present invention have been shown and described, it is to be understood that many changes and modifications may be made thereunto without departing from the spirit and scope of the invention as defined in the appended claims.

What is claimed is:

1. Apparatus for inspecting an edge micro-texture of a semiconductor wafer, comprising
    a diffuse hemisphere having at least one access port and defining a normal axis;
    a laser target sphere mounted within the hemisphere;
    a laser source directing a laser beam to the laser target sphere and forming a laser spot on the laser target sphere, said laser beam being reflected from the laser target sphere;
    a wafer chuck presenting a wafer edge to the reflected laser beam, said wafer edge being tilted from the normal axis; and
    at least one camera for detecting radiation leaving the access port.
2. Apparatus as claimed in claim 1, comprising
    said wafer chuck tilting the wafer edge at approximately 45 degrees from the normal axis.
3. Apparatus as claimed in claim 1, comprising
    means for mounting the laser target sphere at approximately 45 degrees from the access port.
4. Apparatus as claimed in claim 1, comprising
    means for varying the diameter of the laser beam.
5. Apparatus as claimed in claim 1, comprising
    means for varying a cross section pattern of the laser beam.
6. Apparatus as claimed in claim 1, comprising
    means for moving the laser spot on the laser target sphere or on the hemisphere.
7. Method for inspecting an edge micro-texture of a semiconductor wafer, comprising
    directing a laser beam to a laser target sphere which is mounted within a diffuse hemisphere;
    said laser beam forming a laser spot on the laser target sphere; and reflecting said laser beam from the laser target sphere to an edge of the wafer; and
    detecting radiation which leaves the diffuse hemisphere through at least one access port of the diffuse hemisphere with at least one camera.
8. Method as claimed in claim 7, comprising
    varying a diameter of the laser beam.
9. Method as claimed in claim 7, comprising
    varying a cross section pattern of the laser beam.
10. Method as claimed in claim 7, comprising
    moving the laser spot on the laser target sphere or the hemisphere.

11. Method as claimed in claim 7, wherein the laser beam is a bright-field source, only.

12. Method as claimed in claim 7, wherein the laser beam is a dark-field source, only.

13. Method as claimed in claim 7, wherein the laser beam is a continuous diffusive uniform light source.

* * * * *